US 6,602,072 B2

(12) United States Patent
Burney (10) Patent No.: US 6,602,072 B2
(45) Date of Patent: Aug. 5, 2003

(54) DISPOSABLE DEFORMABLE HIGH VOLUME ASPIRATOR (76) Inventor: Debra Burney, 541 County Club Dr., DeFuniak Springs, FL (US) 32435

( * ) Notice: Subject to any disclaimer, the term of this patent is extended or adjusted under 35 U.S.C. 154(b) by 71 days.

(21) Appl. No.: 09/956,709

(22) Filed: Sep. 20, 2001

(65) Prior Publication Data
US 2003/0054317 A1 Mar. 20, 2003

(51) Int. Cl.⁷ .................................. A61C 17/06
(52) U.S. Cl. ...................................... 433/96
(58) Field of Search .......................... 433/96, 92, 95, 433/99, 93, 91

(56) References Cited

U.S. PATENT DOCUMENTS

| | | | |
|---|---|---|---|
| 10,426 A | 1/1854 | Davison | |
| 148,290 A | 3/1874 | Fisk | |
| 2,574,135 A | * 11/1951 | Ward | 433/96 |
| 2,711,586 A | 6/1955 | Groves | |
| 2,885,782 A | 5/1959 | Groves | |
| 3,232,578 A | 2/1966 | Cousins | |
| 3,516,160 A | 6/1970 | Leffler | |
| 3,541,583 A | * 11/1970 | Deuschle | 433/96 |
| 4,083,115 A | * 4/1978 | McKelvey | 433/96 |
| 4,400,168 A | 8/1983 | Buechel et al. | |
| 4,580,978 A | 4/1986 | Moyola et al. | |
| 4,799,885 A | 1/1989 | Hussong | |
| 5,076,787 A | 12/1991 | Overmyer | |
| 5,114,342 A | 5/1992 | Young et al. | |
| 5,509,802 A | 4/1996 | Whitehouse et al. | |
| 5,743,736 A | * 4/1998 | Folko et al. | 433/96 |
| 5,876,384 A | * 3/1999 | Dragan et al. | 604/264 |

* cited by examiner

Primary Examiner—Kevin Shaver
Assistant Examiner—Melba Bumgarner
(74) Attorney, Agent, or Firm—Michael I. Kroll (57) ABSTRACT A deformable disposable high volume aspirator comprising a flexible conduit for the transmission of aspirated fluids, a means for selectively deforming said flexible conduit, a means for diffusing suction during high volume aspiration, and a means for connecting said flexible conduit to a vacuum valve. The present invention overcomes the shortcomings of the prior art by providing an aspirator that is disposable having a flexible deformable conduit member with a malleable metal wire that may be selectively shaped to fit into a patient's mouth whereupon a source of vacuum having been connected to a distal end by means of a connection member and a suction tip on the other distal end can remove a large volume of matter from a patient mouth without lodging onto a patient's cheek or gums that may cause discomfort. The suction tip has a plurality of furcations and a central structure member forming apertures within the suction tip.

1 Claim, 8 Drawing Sheets

DISPOSABLE DEFORMABLE HIGH VOLUME ASPIRATOR

BACKGROUND OF THE INVENTION

1. Field of the Invention

The present invention relates generally to a dental aspirator and, more specifically, to a high volume disposable aspirator having flexible polymeric tubing having a malleable metal wire providing a deformable conduit that may be molded to accommodate a plurality of patients needs and further having a connection member attached at one distal end and a suction tip attached to the other distal end. The suction tip attaches frictionally or adhesively to the end of the tubing having a circular structure with a throughbore and a plurality of forwardly extending furcations connected to a central structure member also having a throughbore that provides strength and support to the furcations. Said furcations providing a plurality of enlarged apertures in between the furcations that allow for the distribution of suction, whereby when a vacuum is applied the particle debris and fluids will be removed without the suction tip becoming lodged to the skin or folds of the mouth causing discomfort. At the tubing's opposing end a connection member of circular structure with a throughbore having a lip on its upper outer circumference is connected to the tubing in the same manner as said suction tip to provide a connection for an existing vacuum source to introduce suction to the interior of the tubing and suction tip.

2. Description of the Prior Art

There are other dental aspirators designed for removing debris. Typical of these is U.S. Pat. No. 10,426 issued to Davison on Jan. 17, 1854.

Another patent was issued to Fisk on Mar. 10, 1874, as U.S. Pat. No. 148,290. Yet another U.S. Pat. No. 2,711,586 was issued to Groves on Jun. 28, 1955 and still yet another was issued on May 12, 1959 to Groves as U.S. Pat. No. 2,885,782.

Another patent was issued to Cousins on Feb. 1, 1966 as U.S. Pat. No. 3,232,578. Yet another U.S. Pat. No. 3,516,160 was issued to Leffler on Jun. 23, 1970. Another was issued to Buechel et al. on Aug. 23, 1983 as U.S. Pat. No. 4,400,168 and still yet another was issued on Apr. 8, 1986 to Motola et al. as U.S. Pat. No. 4,580,978.

Another patent was issued to Hussong on Jan. 24, 1989 as U.S. Pat. No. 4,799,885. Yet another U.S. Pat. No. 5,076,787 was issued to Overmyer on Dec. 31, 1991. Another was issued to Young et al. on May 19, 1992 as U.S. Pat. No. 5,114,342 and still yet another was issued on Apr. 23, 1996 to Whitehouse et al. as U.S. Pat. No. 5,509,802.

The preceding patents are described as follows:

U.S. Pat. No. 10,425: Drawing the saliva from the mouth and keeping it dry during the operation of filling teeth by means of an instrument constructed with a hollow mouth piece A, B, C, which connects with a tube D, and suction and force pump G, in the manner essentially as described.

U.S. Pat. No. 148,290: The saliva-ejector formed by the attachment of the tapered concentric tubes and cheek-outlet to the water-supply pipe, and the flexible tube with its mouth-piece, for insertion in the saliva, all substantially as described and shown.

U.S. Pat. No. 2,711,586: A hand piece forming a vacuum ejector for dental debris, comprising: a tubular body of size to be held in a hand having a suction tip on one end, said suction tip being of small size capable of being inserted directly inside of a dental cavity, means for connecting a vacuum pump to the other side of said body, a first throttling valve in said body manually operable to be set in various positions to change the effective size of the air passageway in said tubular body at the location of said throttling valve, a second interrupter valve in said body having a push button for manual control operative to close the air passageway in said tubular body at the location of said interrupter valve upon depression of said button, said interrupter valve having spring means biasing the same normally to an open position.

U.S. Pat. No. 2,885,782: A hand piece forming a vacuum ejector for dental debris, comprising: a tubular body of size to be held in the hand having a suction tip on one end, said suction tip being of small size capable of being inserted directly inside of a dental cavity, means for connecting a vacuum pump to other end of said body, a throttling valve in said body manually operable to be set in various positions to change the effective size of the air passageway in said tubular body at the location of said throttling valve, an interrupter valve in said body having a push button for manual control operative to relive the suction tip ends of the air passageway from vacuum upon depression of said button, said interrupter valve includes a spring-pressed diaphragm normally closing an air passageway to the outside and susceptible to vacuum conditions in the body thereby automatically opening when the vacuum passes a predetermined limit due to blockage of said suction tip and reliving the vacuum in said body by air passing through said outside air passageway.

U.S. Pat. No. 3,232,578: A dental suction valve comprising in combination: an elongated body member having an internal central fluid passage terminating in an exit opening at one end and an entrance opening at its other end, said body member including a manual holding Handle threadedly connected to the remaining portion of said member adjacent to said one end, the other end of said body member terminating in a nose piece having an inner member terminating in a flat ground surface defined by an arcuate cut out portion, a central portion of said body member including a valve plate threadedly connected to said handle on one end, the other end of said valve plate terminating in a flat smoothly ground surface juxtaposed said flat ground surface of said nose piece; and a valve disk having flat opposite smoothly ground surfaces positioned in said arcuate cut out portion so that its axis runs parallel to and spaced from the longitudinal axis of said body member, and its opposite surfaces are in fluid tight engagement with said smoothly ground surfaces of said nose piece and valve plate, a peripheral portion of said disc extending from the side of said body member to be exposed so that it may be manually rotated to rotate said disk about its own axis, said disk including an off-center opening adapted to register with said central fluid passage when in a first position and to be moved out of registration with said fluid passage so that another portion of said disk blocks said fluid passage when said disk is rotated to a second position, a portion of said disk includes a curved opening; screws for securing said valve plate to said nose piece, one of said screws passing through said curved opening to function as a stop and thereby limit rotation of said disk between said first and second positions.

U.S. Pat. No. 3,516,160: A dental aspiring cuspidor to be placed in a patients mouth for ejecting saliva, water and foreign matter therefrom. The aspirating cuspidor comprises an open-ended, tubular housing having a first end adapted to be connected to a source of suction and a second end adapted for the reception of saliva, water and foreign matter and providing an internal ejecting passageway between the ends of sufficient volume to accommodate rapid flow of saliva, water and foreign matter therethrough. The housing includes venting port means between the ends for creating an aspirating suction through the second end of the housing and for avoiding excessive and discomforting suction to the patients mouth. The dental aspirating cuspidor further includes a removable and replaceable ejecting member frictionally secured in the second end of the housing and adapted to be placed in the patient's mouth for ejecting the saliva, water and foreign matter therefrom and adapted to be removed from the housing and replaced after use by a patient.

U.S. Pat. No. 4,400,168: Surgical suction apparatus for applying suction to surgical debris to clear a surgical wound and including structure for clearing any surgical debris lodged in the entrance aperture of the apparatus and which structure may also be used to vary the effective size of the entrance aperture to vary the suction applied to the surgical debris.

U.S. Pat. No. 4,580,978: A vacuum operated dental high volume evacuation system is provided wherein an extraction instrument is connected to a debris collector for solids which in turn is connected to a separator unit wherein the liquid in the evacuated material is separated from the vacuum air and the dry vacuum air is directed to the vacuum source unit which creates the vacuum for the system. The separator unit includes a vacuum chamber positioned above a drainage chamber with a valve disposed therebetween. The drainage chamber is normally maintained at atmospheric pressure and the valve is normally closed due to the pressure differential between the two chambers. A liquid level sensor is provided in the vacuum chamber to sense the rise of liquid therein which upon reaching a certain level trips the sensor which results in an equalization of vacuum pressure between the two chambers and the draining of the liquid in the vacuum chamber into the drainage chamber. Upon the deactivation of the liquid level sensor, the drainage chamber is returned to atmospheric pressure and the valve between the two chambers closed as a result of the pressure differential.

U.S. Pat. No. 4,799,885: An improved dental suction device is disclosed comprising a suction line and automatic, orientation-responsive switching means adapted to provide suction at the inlet when the device is aligned in a first operative orientation and turn off the suction at the inlet when aligned in a second standby orientation.

U.S. Pat. No. 5,076,787: A variable suction aspirator head for an end fitting of a suction hose consisting simply of an inner valve tube having wall holes and a slideable outer barrel, permitting variations in suction, the trapping of solid material by the valve tube wall holes and easy disassembly for cleaning and sterilization of the parts after each use.

U.S. Pat. No. 5,114,342: A saliva ejector tip for dental use comprises a tube (10) with a pliable, flexible tip. The end (26) of the tip is flat. The sides of the tip adjacent the end extend down to form a cage (22) of spiral mullions which terminate at a solid base portion of the tip. Extending axially inside the tip from the end is an internal plunger (24). Below the plunger on the inside is an annular valve seat (28). When the end is pushed in, the cage collapses and the plunger is pushed into the valve seat which it closes off so as to close the tip. In this manner the tip can be closed with one hand when it is removed from the mouth, thereby to avoid a sucking sound, and the need for the dentist to handle and contaminate the more proximal hose and hose valve, which are difficult to sterilize. The mullions of the cage can be extended down over the base of the tip (FIG. 4) to provide lands (32) on the base for an easier grip and saliva routing action.

U.S. Pat. No. 5,509,802: An oral suction tip is described which includes a tubular body. The tubular body has a peripheral sidewall, a first end, a second end, and a single passage for transmitting fluids extending between the first end and the second end. A mouthpiece is provided at the second end of the tubular body. At least one vacuum release aperture extends through the sidewall of the tubular body in direct communication with the fluid passage. The at least one vacuum release aperture is spaced from the mouthpiece, such that when the mouthpiece is inserted into a patient's mouth the at least one vacuum release aperture is not confined within the patient's mouth. A porous guard overlies in spaced relation the at least one vacuum release aperture. This prevents accidental blockage of the at least one vacuum release aperture and also prevents regulation of the suction by means of the at least one vacuum release aperture.

While these dental aspirators may be suitable for the purposes for which they were designed, they would not be as suitable for the purposes of the present invention, as hereinafter described.

SUMMARY OF THE PRESENT INVENTION

A primary object of the present invention is to provide a disposable aspirator capable of removing high volumes of saliva, water and other particle matter from a dental patient's mouth without discomfort.

Another object of the present invention is to provide an aspirator with a flexible conduit.

Yet another object of the present invention is to provide an aspirator with a malleable metal wire within the wall whereby the flexible tube can be selectively deformed.

Still yet another object of the present invention is to provide an aspirator with a suction tip with a throughbore formed by a plurality a central structure member furcated at one end forming suction apertures in the suction tip.

Another object of the present invention is to provide an aspirator with a suction tip that will not attach by suction to a patient's cheek or gums.

Yet another object of the present invention is to provide an aspirator having a connection member with a throughbore having a lip for attaching thereon a vacuum source.

Additional objects of the present invention will appear as the description proceeds.

The present invention overcomes the shortcomings of the prior art by providing an aspirator that is disposable having a flexible deformable conduit member with a malleable metal wire that may be selectively shaped to fit into a patient's mouth whereupon a source of vacuum having been connected to a distal end by means of a connection member and a suction tip on the other distal end can remove a large volume of matter from a patient mouth without lodging onto a patient's cheek or gums that may cause discomfort. The suction tip has a plurality of prongs and a central structure member forming apertures within the suction tip.

The foregoing and other objects and advantages will appear from the description to follow. In the description reference is made to the accompanying drawing, which forms a part hereof, and in which is shown by way of illustration specific embodiments in which the invention may be practiced. These embodiments will be described in sufficient detail to enable those skilled in the art to practice the invention, and it is to be understood that other embodiments may be utilized and that structural changes may be made without departing from the scope of the invention. In the accompanying drawing, like reference characters designate the same or similar parts throughout the several views.

BRIEF DESCRIPTION OF THE DRAWING FIGURES

In order that the invention may be more fully understood, it will now be described, by way of example, with reference to the accompanying drawing in which.

DESCRIPTION OF THE REFERENCED NUMERALS

Turning now descriptively to the drawings, in which similar reference characters denote similar elements throughout the several views, the Figures illustrate the high volume disposable aspirator of the present invention. With regard to the reference numerals used, the following numbering is used throughout the various drawing figures.

10 deformable disposable high volume aspirator
12 patient
14 patients mouth
16 flexible conduit
18 wire member
20 sidewall of 16
22 evacuation channel
24 first end of 16
26 second end of 16
28 furcated suction head
30 housing of 28
32 suction channel
34 first end of 28
36 second end of 28
38 furcation
40 evacuation recess
42 retaining flange
44 suction tip
45 central recess of 44
46 vacuum connection member
48 vacuum valve
50 vacuum channel
52 first end of 46
54 second end of 46
56 annular ring
62 male portion of 46

DETAILED DESCRIPTION OF THE PREFERRED EMBODIMENTS

The following discussion describes in detail one embodiment of the invention and several variations of that embodiment. This discussion should not be construed, however, as limiting the invention to those particular embodiments. Practitioners skilled in the art will recognize numerous other embodiments as well. For a definition of the complete scope of the invention, the reader is directed to the appended claims.

Figure 1:
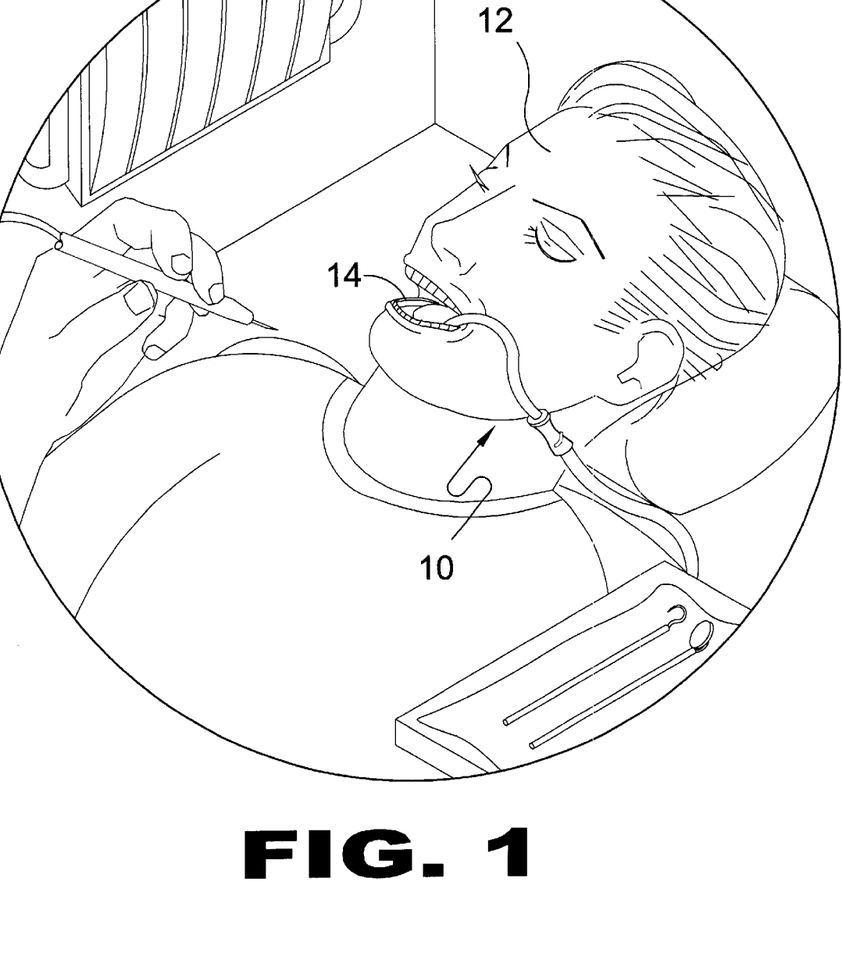
FIG. 1 is an illustrative view of the present invention in use.

FIG. 1 is an illustrative view of the present invention in use. Shown is the present invention 10 in use wherein the disposable high volume aspirator can be placed in the mouth 14 of a patient 12 in any location needed and shaped accordingly due to the flexible conduit 16, to aid a dentist or other professional in the removal of a high volume of particle matter and fluids from a patients mouth such as amalgam, large portions of calculus, saliva and tooth fragments, without causing any discomfort to the patient by preventing the application of suction to the gums or cheek.

Figure 2:
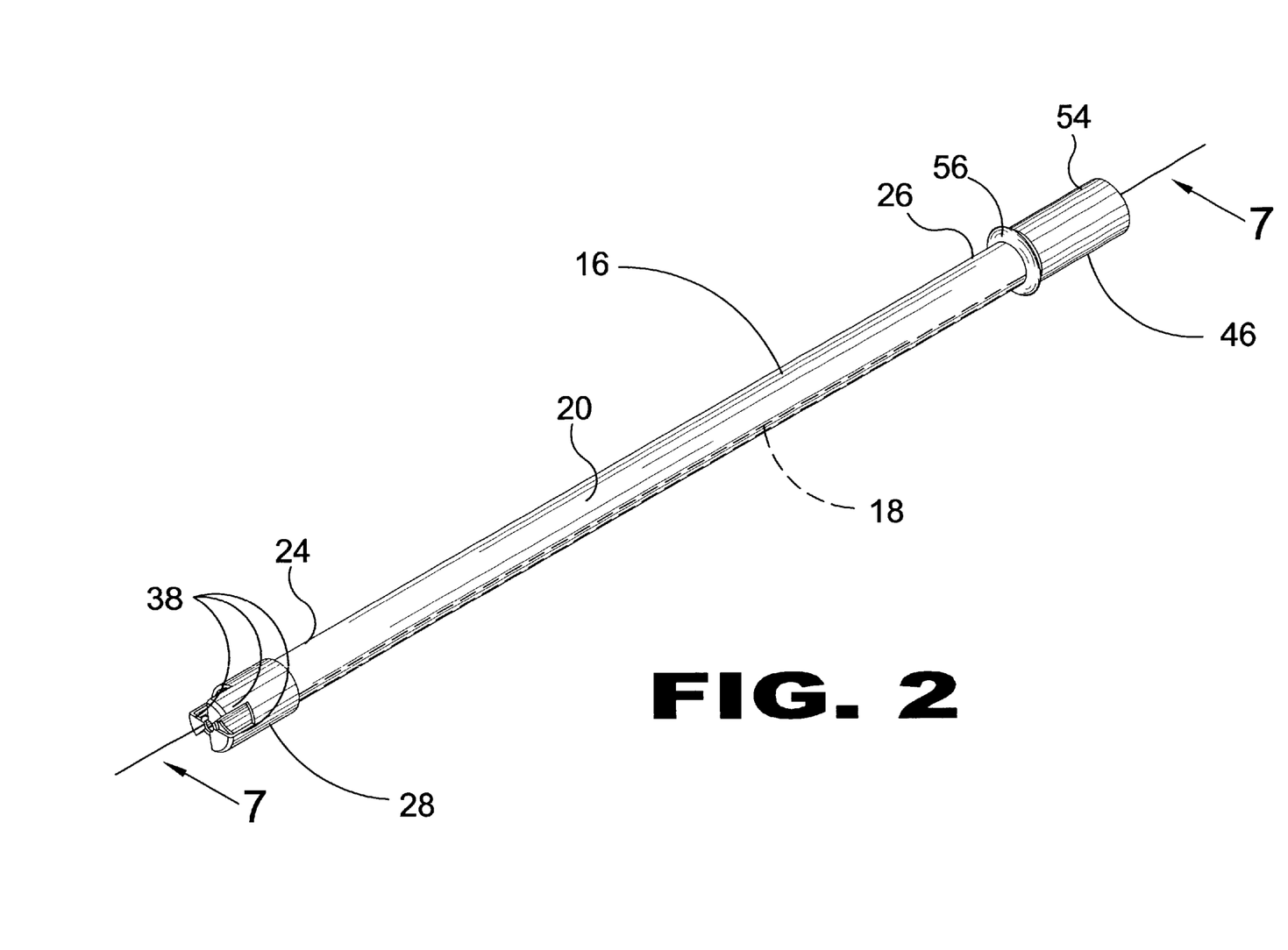
FIG. 2 is a perspective view of the present invention.
Figure 3:
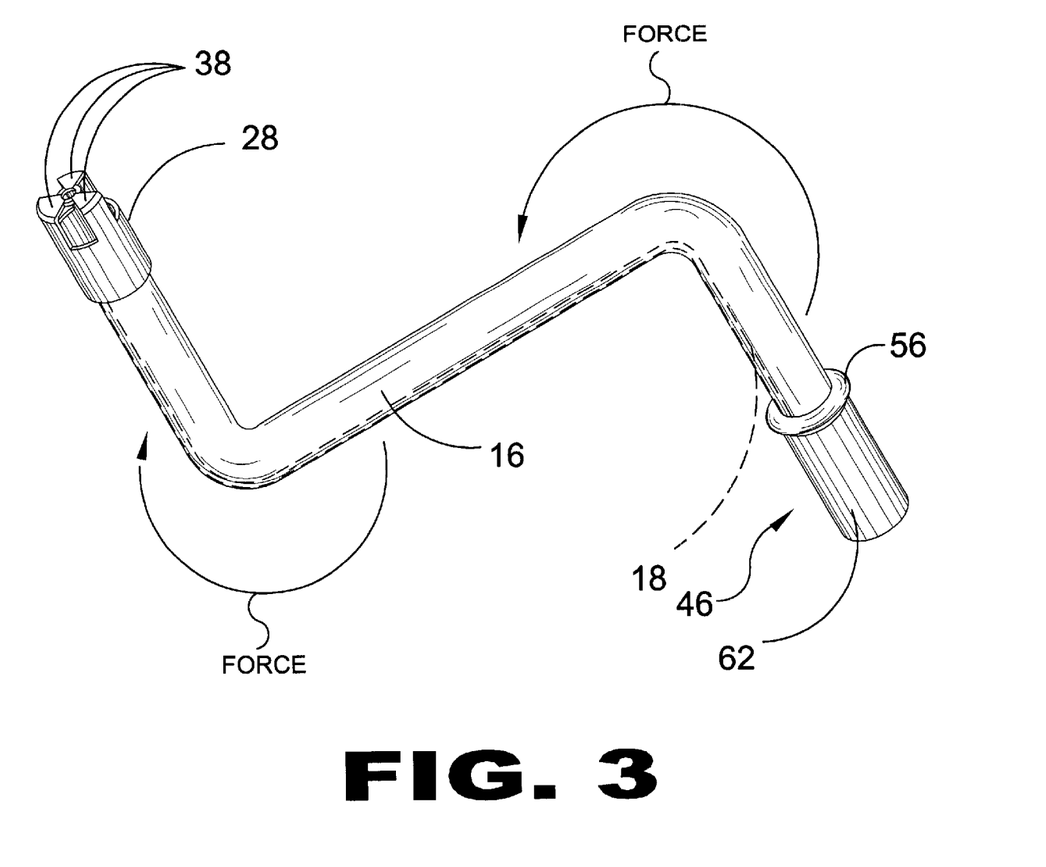
FIG. 3 is a perspective view of the present invention.
Figure 8:
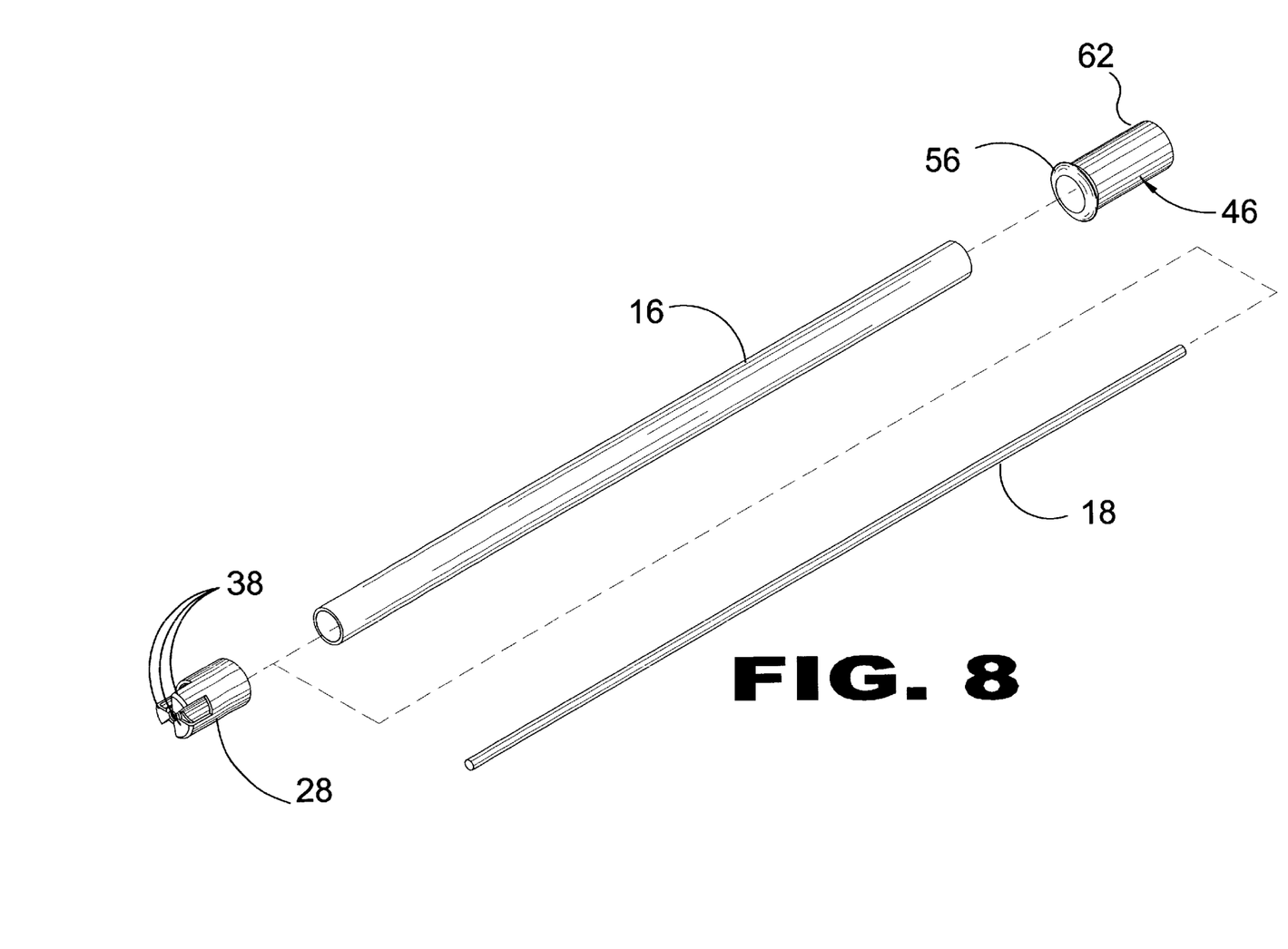
FIG. 8 is an exploded view of the present invention.

FIGS. 2 and 3 are perspective views of the present invention. Shown is a flexible conduit 16 comprising a flexible tubular sidewall 20 having a first end 24, a second end 26, an evacuation channel extending therethrough, and a malleable wire member 18 extending longitudinally end-to-end, a suction head 28 is attached to the first end 24 thereof and a vacuum connection member 46 is attached to said second end 26 thereby establishing a flexible, deformable suction conduit 10 capable of repeated reforming. A male portion of the vacuum connection member 62 is inserted into an existing vacuum valve 48 until the annular ring 56 prevents further entry therein. The interrelationship of the aforementioned components could be better understood when viewing the exploded view of the present invention 10 shown in figure 8.

FIG. 3 demonstrates the flexible conduit 16 selectively shaped from the linear form shown in FIG. 2. Housed within the sidewall 20 of the flexible conduit 16 is a malleable wire member 18 providing a means to deform and contort the structure of the flexible conduit 16 into a semi-permanent configuration for appropriate placement inside a patients mouth 14.

Figure 4:
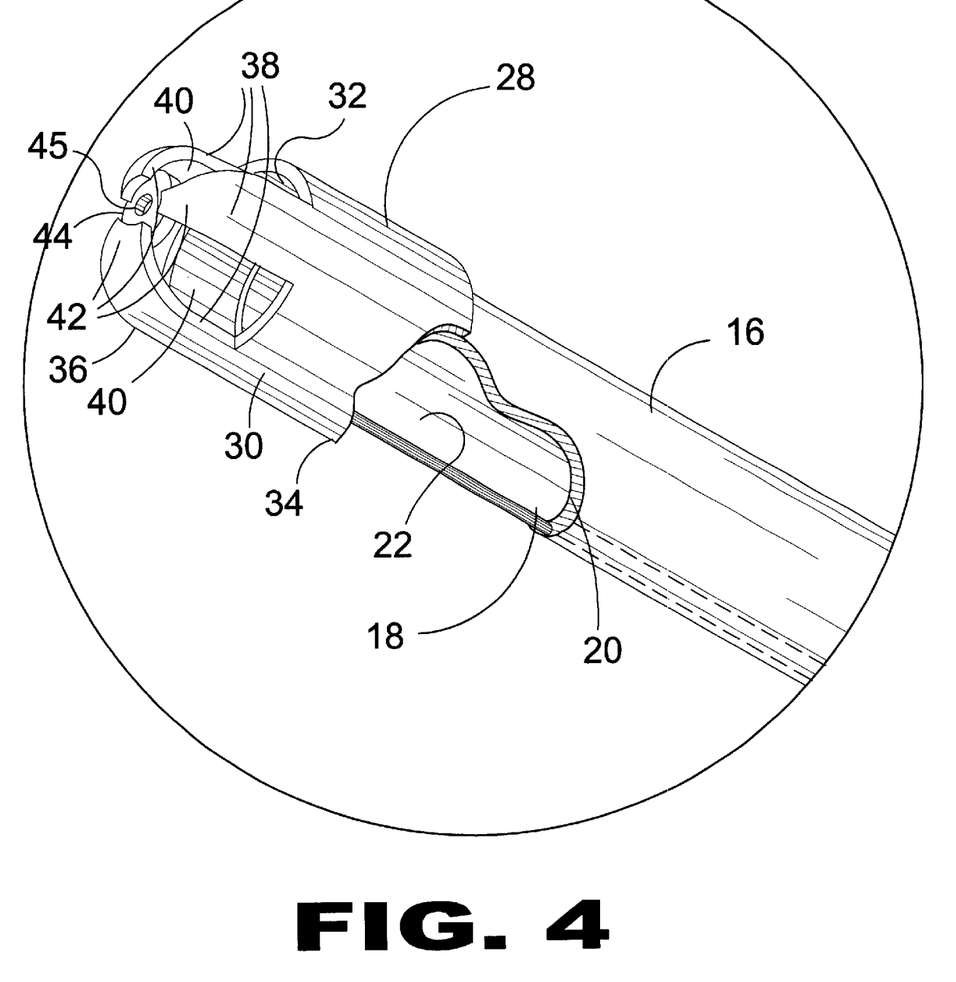
FIG. 4 is a cut away view of the present invention.
Figure 5:
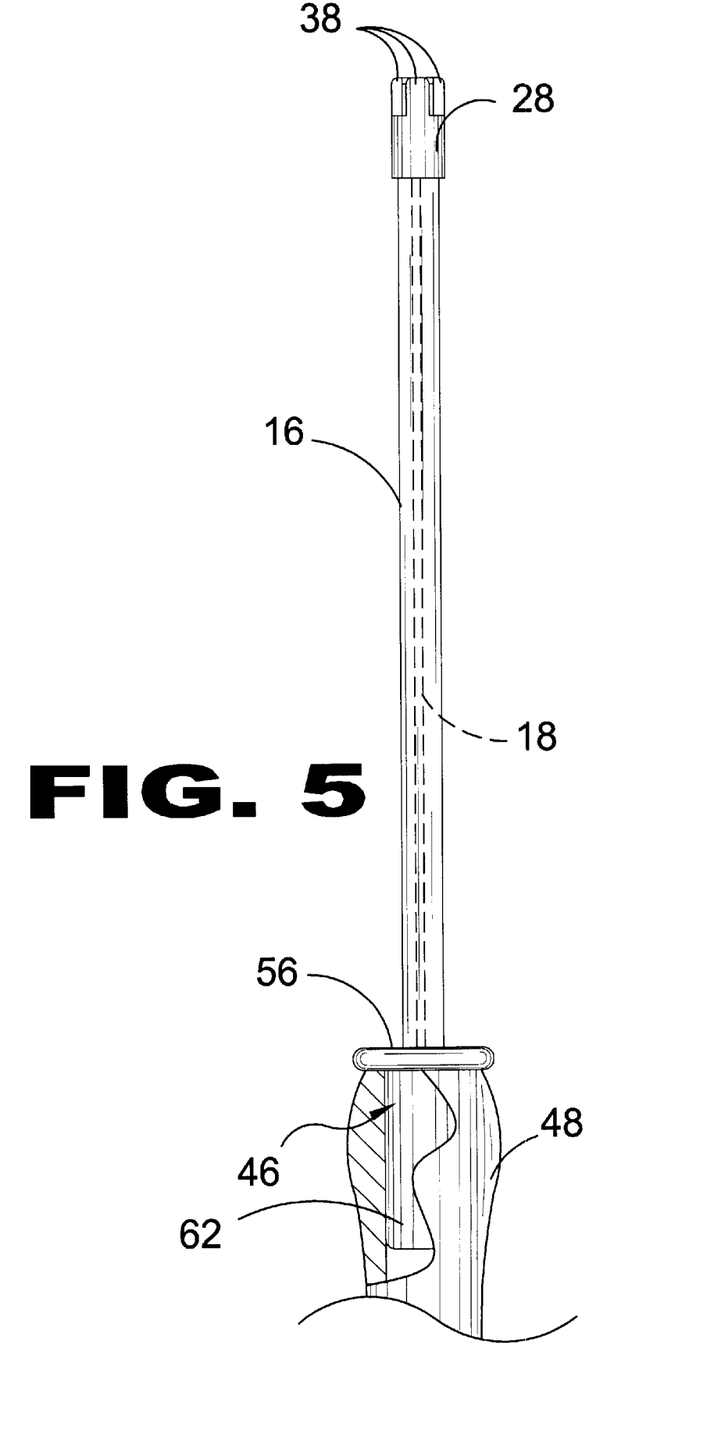
FIG. 5 is a side cut away view of the present invention.
Figure 6:
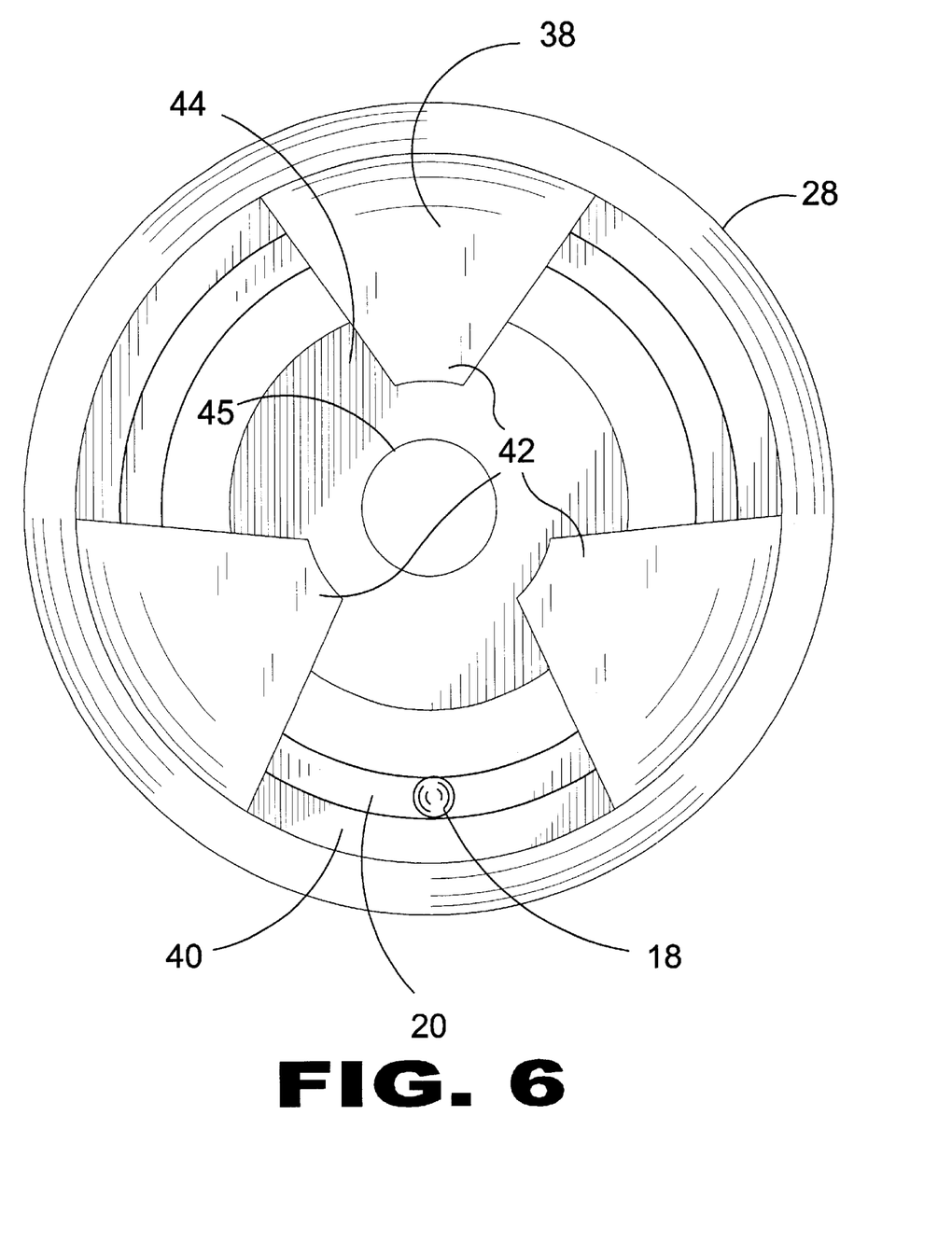
FIG. 6 is a top view of the present invention.
Figure 7:
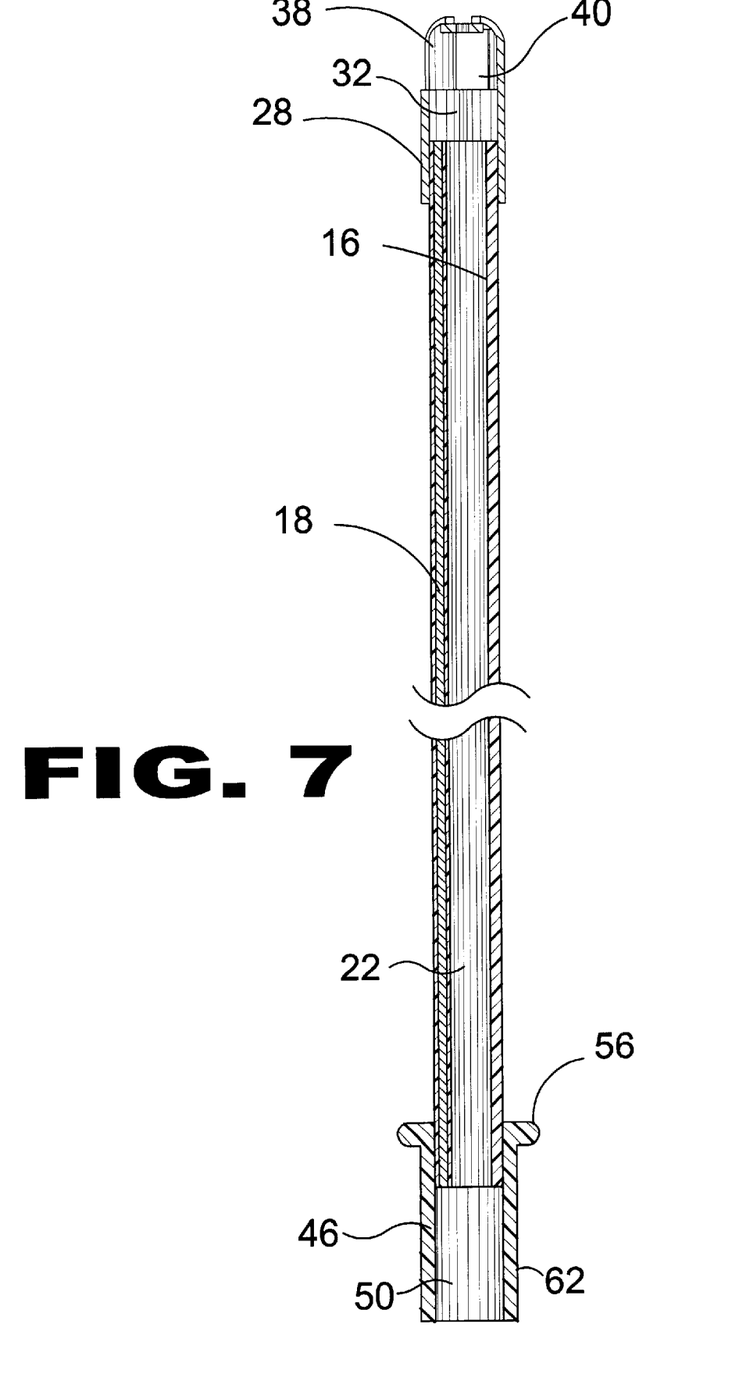
FIG. 7 is a cross section of the present invention.

FIG. 4 is a cut away view of the present invention showing a portion of the flexible conduit 16 cut away to reveal the wire member 18 contained therein and forming an integral part therewith used to provide semi-permanent maintenance of any bends or deformations made to the tube's shape. FIGS. 4 and 6 depict the furcated suction head 28 having a substantially cylindrical housing 30 with a plurality of furcations 38 forwardly extending and forming evacuation recesses 40 therebetween and further having retaining flanges 42 projecting medially therefrom to maintain a suction tip 44 with a central recess 45 passing therethrough to provide a suction head 28 having a plurality of enlarged professional applications. The housing 30 has a first end 34 wherein the flexible conduit 16 is inserted into the suction channel 32 therein and an opposite end that has evacuation recesses 40 and a suction tip 44 with a central recess 45 for removing fluid and material from a patients mouth 14.

It will be understood that each of the elements described above, or two or more together may also find a useful application in other types of methods differing from the type described above.

While certain novel features of this invention have been shown and described and are pointed out in the annexed claims, it is not intended to be limited to the details above, since it will be understood that various omissions, modifications, substitutions and changes in the forms and details of the device illustrated and in its operation can be made by those skilled in the art without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed is new and desired to be protected by Letters Patent is set forth in the appended claims:

1. A deformable disposable high volume dental aspirator comprising:
   a) a flexible conduit for the transmission of aspirated fluids comprising a tubular peripheral sidewall and an evacuation chamber formed by said sidewall;
   b) a means for selectively deforming said flexible conduit comprising a resilient wire member that is longitudinally integral with said conduit and provides semi-rigid characteristics thereto allowing a user to quickly and easily manipulate said conduit into a desired shape and have it remain in that shape until further manipulation by the user;
   c) a means for diffusing suction during high volume aspiration comprising a substantially cylindrical peripheral housing, a suction channel formed by said housing, a first end of said housing for sealably engaging with said flexible conduit, furcations projecting longitudinally toward a second end of said housing, evacuation recesses formed between said furcations, and retaining flanges extending medially from the distal ends of each said furcation terminating such as to form a central opening communicating with said evacuation recesses;
   d) a substantially disc-shaped suction tip member mounted inside said housing adjacent said flanges such that said flanges overlap and hold in place said suction tip member, said suction tip member having a central recess passing therethrough; and
   e) means for connecting said flexible conduit to a vacuum valve.

\* \* \* \* \*